Figure 1:
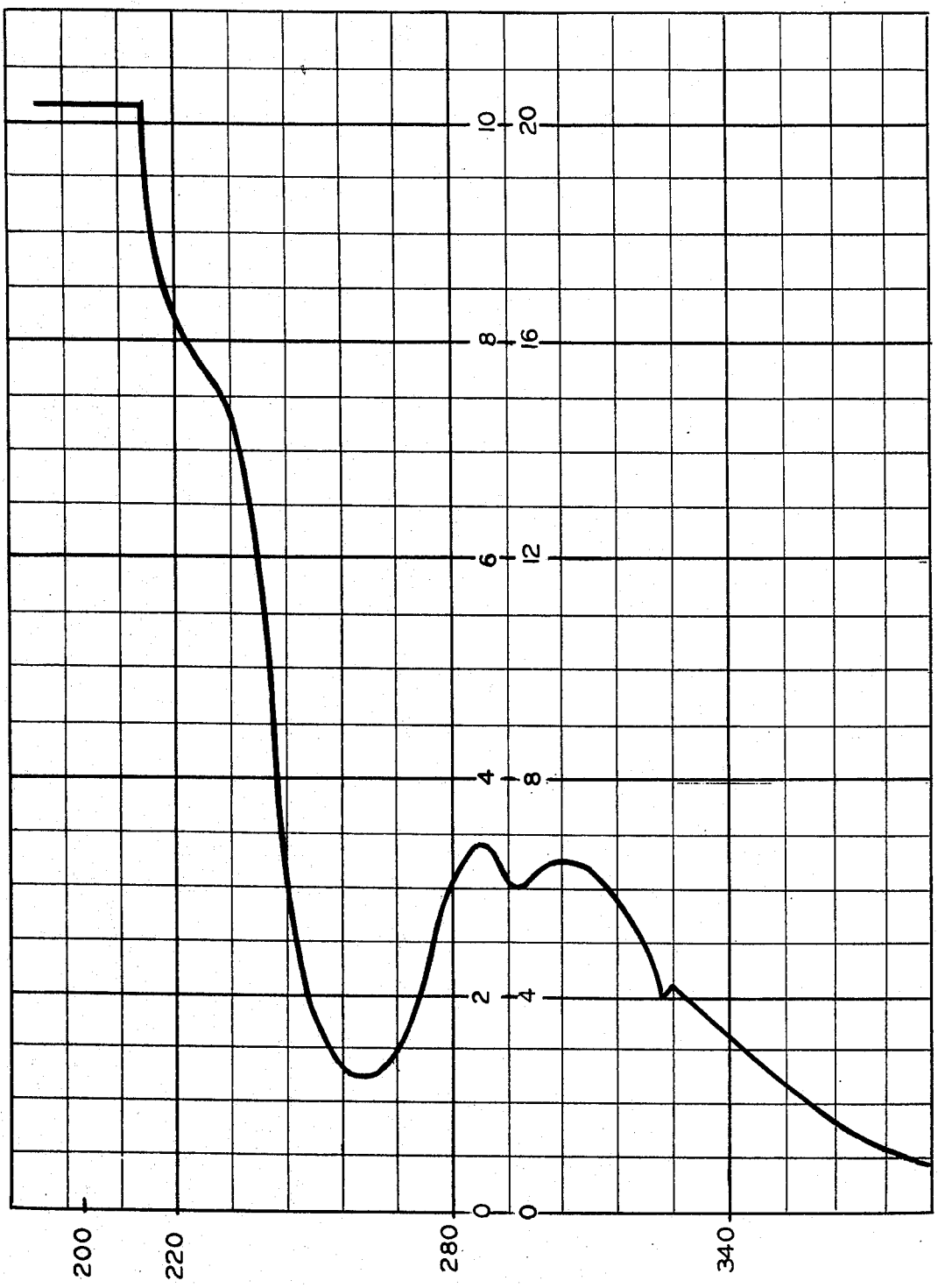

United States Patent [19]

Madaus et al.

[11] 3,997,671
[45] Dec. 14, 1976

[54] SILYBIN POLYMERS AND THERAPEUTIC COMPOSITIONS

[75] Inventors: Rolf Hermann Heinrich Madaus, Cologne-Bruck; Günter Halbach, Cologne; Wilfried Trost, Bensberg-Frankenforst, all of Germany

[73] Assignee: Dr. Madaus & Co., Cologne, Germany

[22] Filed: Apr. 4, 1975

[21] Appl. No.: 565,175

[30] Foreign Application Priority Data

Apr. 4, 1974 Germany .......................... 2416302

[52] U.S. Cl. .............................. 424/278; 260/340.3
[51] Int. Cl.[2] ....................................... C07D 319/20
[58] Field of Search ................. 260/340.3; 424/278

[56] References Cited
FOREIGN PATENTS OR APPLICATIONS 1,963,318   6/1971   Germany ........................... 424/278

OTHER PUBLICATIONS

C.A. 72;31714(b).

Primary Examiner—Ethel G. Love
Attorney, Agent, or Firm—Burgess, Dinklage & Sprung

[57] ABSTRACT

New, highly effective therapeutic polymers of oligomers of Silybin are provided as well as a process for making same employing organic solvent/mineral acid systems in which Silybin auto-condenses to oligomers thereof having polymerization numbers of, e.g., 2 to 8.

14 Claims, 4 Drawing Figures

FIG. I.

SILYBIN POLYMERS AND THERAPEUTIC COMPOSITIONS

The invention relates to novel therapeutic compisitions. More specifically, the invention provides new polymeric intermolecular condensation products of Silybin (Silymarin I), processes for the preparation thereof, and pharmaceutical compositions containing such products.

Silybin has been assigned the names 3,5,6-trihydroxy-2-[2-(4-hydroxy-3-methoxyphenyl)-3-(hydroxymethyl)-1,4-benzodiozan-6-yl]-4-chromanone or 3,5,7-trihydroxy-2-[3-(4-hydroxy-3-methoxyphenyl)-2-(hydroxymethyl)-1,4-benzodioxan-6yl]-4-chromanone, i.e., to have the following structural formula:

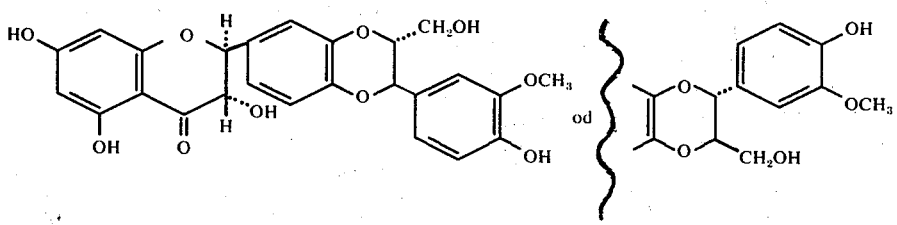

Silybin (Silymarin I) is known to be one of the few hormones that possess etiologically curative action in liver diseases, e.g., hepatophylactic activity, Pelter, A. and Hansel, Tetrahedron Letters, 25, 2911(1968), Wagner, H., Horhammer, L., Munster, R., "Arzneimittel-Forschung" 18, 688 (1968) German Offenlegungsschrift No. 1,923,082 of Dr. Madaus & Co., German Offenlegungsschrift 1,767,666 of Dr. Madaus & Co. Hahn, G. and collaborators (Madaus), "Arzneimittel-Forschung" 18,698 (1968).

There has been a need for compounds having a many times stronger pharmacological, etiotropic action, both as regards the intensity of the action and in breadth of application in diseases of the liver, to enable the protective and stabilizing effect on the liver cells to be intensified. Specifically although Silybin is known to have good hepatophylactic action, there is a need for a still more effective drug, since diseases of the liver are becoming more common.

The present invention provides new compounds having a many times stronger pharmacological hepatophylatic action than the known compounds (such as Silybin, for example).

It has now been found, surprisingly, that certain new polymers of Silybin display such higher activity and the present invention provides polymeric intermolecular condensation products of Silybin and salts thereof.

The invention also provides a process for preparing the said Silybin polymers comprising the polymerization of Silybin in the presence of a mineral acid in a suitable organic solvent, by acid-catalyzed, intermolecular autocondensation; suitable solvents are those in which the Silybin is still sufficiently soluble, even the presence of aqueous mineral acids, that no precipitation of the monomeric starting product takes place during the reaction. The presence of a mineral acid is necessary for autocondensation of Silybin to take place. The invention additionally provides therapeutic compositions containing the new, specified polymers.

The preparation of the polymers of Silybin is difficult. Under alkaline conditions no polymers at all could be obtained and the polymerization of Silybin in acid solution at first presented great difficulties, since Silybin is soluble only with extreme difficulty in most organic solvents in the presence of aqueous mineral acids.

Surprisingly, organic solvent-mineral acid systems have been found in which the polymerization is easily possible as an acid-catalyzed intermolecular autocondensation. The Silybin must still be so easily soluble, even in the presence of aqueous mineral acids, that no precipitation of the monomeric starting product takes place during the reaction time, and therefore only solvents with which this can be accomplished must be used in accordance with the invention for the reaction. The cyclic ethers, dioxane and tetrahydrofuran have proven to be especially suitable. Hydrochloric acid or sulfuric acid are preferred as the mineral acids, although other mineral acids can also be used, such a phosphoric acid, for example.

Hydrochloric acid is used preferentially, because being a volatile acid, it is easiest to remove in the refinement of the intermolecular condensation products. In accordance with the invention, the higher the acid concentration in the reaction medium is, the more rapidly the autocondensation will take place.

A solvent system consisting of dioxane and concentrated hydrochloric acid has proven to be especially suitable. It has been found that after only 24 to 48 hours of reaction time at room temperature the Silybin was transformed to the new compounds, which are designated polymers on the basis of their physicochemical properties.

The longer the reaction mixture is let stand at room temperature, the greater is the degree of polymerization. Specifically, the following values were found in the first experiments in this regard:

1. Silybin, dissolved in a mixture of dioxane and concentrated hydrochloric acid; reaction time at room temperature: 2 weeks; average molecular weight 820.
2. Same as 1, but 4 weeks of reaction time; average molecular weight 1608.

The molecular weight determinations were performed osmometrically in acetone.

From this data it appears that Silybin is polymerizable or condensable in acid solution, the degree of polymerization depending on the reaction time.

The monomeric compound described polymerizes with dehydrogenation, i.e., the polymer forms from two or more molecules joined together by oxidation. It is difficult to conduct the polymerization reaction in such a manner that a specific degree of polymerization is achieved, and that the reaction product will be obtained pure and free of starting substances, other polymers or decomposition products, or heterogeneous polymers, but it is possible to achieve stability in the polymer at a specific polymerization number. In accordance with the invention it is possible to polymerize or condense Silybin to new polymer compounds under precise control and this represents a significant advance.

For the performance of the process of preparation, a specific amount of the monomeric compound is dissolved in an organic solvent such as dioxane of tetrahydrofuran, to form an 0.5 to 2% solution. Concentrated to fuming hydrochloric acid of 12N sulfuric acid is added to this solution. The reaction product is let stand for 4 to 24 days and then water is added and the precipitate which settles upon the addition of water is removed by filtration and washed acidfree with water and dried under reduced pressure at a temperature between 40° and 50° C.

In accordance with the invention, polymers and oligomers having a polymerization degree of $n = 2$ to $8$ can be obtained, i.e., dimers, trimers, tetramers, pentamers, hexamers, heptamers and octamers. Preferably $n$ will be equal to from 2 to 6, especially from 2 to 4, $n = 2$ to 3 being especially advantageous for use as a medicament. The degree of polymerization increases in proportion to the reaction time and the acid concentration.

The degree of polymerization is determined by determining the molecular weight osmometrically in acetone. The theoretical and found values agree within the usual limits if one assumes the theoretical value of the molecular weight to be based on two or more monomeric molecules linked together by oxidation. These polymers are generally not crystallizable, but they can be refined by reprecipitation from an acetone and water system (including treatment with active charcoal if desired) to a colorless, amorphous product. Refinement can also be performed in a silica gel-G column using a mixture of n-propanol and water (7:3 parts, by volume) as the elutant. The chromatographic purity of the substance is tested with the same fluid on silica gel-G plates. The detection is performed with 2,4-dinitrophenylhydrazine.

The formation of water-soluble salts of the polymers of the invention, such as an N-methylglucamine salt for example, can be performed by using an excess of N-methylglucamine (the higher the degree of polymerization, the greater the excess must be) on the monomeric compound, dissolved with heating in methanol, followed by the complete removal of the solvent by distillation under reduced pressure, after which the residue is dried in the vacuum dryer at a maximum of 45° C.

The polymeric compounds of the invention have an antihepatotoxic action which is significantly higher than that of the monomers. The results obtained with intravenously administered synthetic polymer compound, in the form of its N-methylglucamine salts for example, indicate a surprising, many times stronger, pharmacological action in comparison to the monomeric form. The therapeutic daily dose for human beings is 50 to 150 mg per day, according to the severity of the disorder and the individual constitution.

The toxicity and the pharmacological effectiveness of the new reaction products as medicinal preparations has been determined.

In mice, the acute toxicities of the monomers, dimers and trimers of Silybin (Silymarin I) (hereinafter referred to as SIP) were determined on the basis of intravenous injections of the substance as N-methylglucamine salts.

SUBSTANCES AND SOLUTIONS FOR THE DETERMINATION OF ACUTE TOXICITY

1. Silybin dimer as N-methylglucamine salt SIP MG 16 (Molar ratio of Silybin dimer to N-methylglucamine 1 : 6)
220 mg SIP MG 16 = mg Silybin dimer
Stock solution:
  1.5 g SIP MG 16 in 50 ml of 0.9% NaCl solution plus 4% PVP (polyvinylpyrrolidone)
Dosages:
  0.60 g / 20 ml 0.9% NaCl sol. + 4% PVP / kg I.V.
  0.50 g / 20 ml 0.9% NaCl sol. + 4% PVP / kg I.V.
  0.42 g / 20 ml 0.9% NaCl sol. + 4% PVP / kg I.V.
  0.36 g / 20 ml 0.9% NaCl sol. + 4% PVP / kg I.V.

2. Silybin trimer as N-methylglucamine salt SIP MG 118 (Molar ratio of Silybin dimer to N-methylglucamine 1 : 18)
318 mg of SIP MG 118 = 100 mg of Silybin trimer
Stock solution:
  1.8 g SIP MG 118 in 60 ml of 0.9% NaCl solution plus 4% PVP
Dosages:
  0.60 g / 20 ml 0.9% NaCl sol. + 4% PVP / kg I.V.
  0.50 g / 20 ml 0.9% NaCl sol. 30 4% PVP / kg I.V.
  0.42 g / 20 ml 0.9% NaCl sol. + 4% PVP / kg I.V.
  0.36 g / 20 ml 0.9% NaCl sol. + 4% PVP / kg I.V.
  0.30 g / 20 ml 0.9% NaCl sol. + 4% PVP / kg I.V.

3. Polyvinylpyrrolidone (PVP) Mol. wt. 10,000

METHOD

The experimental animals were female and male mice, strain NMRI of the Voss company of Tuttlingen, Germany, weight approximately 20 to 25 g. Under identical ambient conditions, all animals were given "Ssniff" standard feed and drinking water ad libitum.

The test substances were injected into the mice in a volume of 20 ml of 0.9% NaCl solution plus 4% PVP per kilogram intravenously, at a rate of injection of approximately 1 ml per minute. The observation time was 14 days. 10 female and 10 male animals were used per dose.

RESULTS AND EVALUATION

In mice the $LD_{50}$ for the N-methylglucamine salt of the dimer Silybin is $450 + 22$ mg/kg SIP MG 16 I.V. = 204.5 kg/kg Silybin dimer for female animals and $520 \pm 9$ mg/kg SIP MG 16 I.V. = 263.3 mg/kg Silybin dimer for male animals. The corresponding values for the N-methylglucamine salt of the silybin trimer are: $300 \pm 10$ mg/kg SIP MG 118 I.V. = 94.34 mg/kg Silybin trimer for female mice and $330 \pm 10$ mg/kg SIP MG 118 I.V. = 103.77 mg/kg Silybin trimer for male mice.

The testing of the pharmacological effectiveness of the polymers of the invention was performed on the basis of the phalloidin liver damage model. The antiphalloidin action of these substances in the form of N-methylglucamine salts injected intravenously is taken as the index of pharmacological effectiveness.

THE ACTION OF SILYBIN DIMER AND TRIMER

The substances used for comparison were:
a. Silybin monomer as the N-methylglucamine salt;
b. methylglucamine.

The Silybin dimer and trimer were used in the experiment in the form of N-methylglucamine salts.

SUBSTANCES AND SOLUTIONS

1. Silbin dimer 11.0 mg/kg SIP MG 16 I.V. = 5 mg/kg Silybin dimer
22.0 mg/kg SIP MG 16 I.V. = 10 mg/kg Silybin dimer
2. Silybin trimer
   15.9 mg/kg SIP MG 118 I.V. = mg/kg Silybin trimer
   31.8 mg/kg SIP MG 118 I.V. = 10 mg/kg Silybin trimer
3. Silybin monomer
   140.5 mg/kg SI MG 11 I.V. = 100 mg/kg silybin
4. N-methylglucamine (MG)
   21.8 mg/kg I.V.
5. Polyvinylpyrrolidone (PVP)
   Mol. wt. 10,000
6. Phalloidin
   3 mg of phalloidin, predissolved in 3 ml of methanol, to 20 ml of 0.9% NaCl solution per kg I.P.

The substances 1 to 4 were dissolved in 20 mol ofj 0.9% NaCl solution plus 4% PVP.

Method

The experimental animals were female SPF mice, strain NMRI of Voss of Tuttlingen. Germany, weighing approximately 25 g. Under identical ambient conditions, all animals received Ssniff standard feed and drinking water ad libitum. The test substances were injected intravenously 1 hour before phalloidin poisoning (3 mg/kg I.P.). The control animals received the corresponding amount of N-methylglucamine intraveneously. The mortality rate and survival rate after phalloidin liver damage were recorded. The observation time was 7 days. 20 animals were used per group.

Results and Evaluation: See Table 1, below.

As it appears from the table, 85% of the mice treated with N-methylglucamine (controls) and poisoned 1 hour later with 3 mg/kg phalloidin IP. In the same test, Silybin monomer treatment in a dose of 100 mg/kg I.V. (administered as the N-methylglucamine salt reduces the mortality rate to 30%. Silybin dimer and trimer, in a dose of 10 mg/kg I.V. (also as N-methylglucamine salt), completely prevent the death of the animals. At the dose of 5 mg/kg I.V., only 10 and 5%, respectively, of the animals are killed. Silybin (Silymarin I), in the form of its polymers, achieves a decided improvement of its prophylactic against the deadly phalloidin poisoning of mice.

The following examples, illustrate, without limitation, various embodiments of the invention.

EXAMPLE 1

Prepartion of the Dimer of Silybin 10 g of Silybin (Silymarin I) (German Offenlegungsschrift No. 1,923,082) were dissolved in 2 liter of dioxane and to this folution there was added one liter of 37% (fuming) hydrochloric acid. The reaction mixture was let stand for 4 days at room temperature and then was diluted with 7 liters of water. The beige-colored precipitate that settled out was easily removed by filtration. IT was washed acid-free with water and dried under reduced pressure at 40° C. The yield was 8.2 g. The product had a molecular weight of 943 (determined osmometrically in acetone). The theoretical molecular weight of two oxidatively linked Silbyin molecules is reckoned at 963. The Silybin dimer is not crystallizable, but it can be refined by reprecipitation from an acetonewater mixtire (plus treatment with active charcoal if desired) to a colorless, amorphous product. Refinement can also be effected on a silica gel-G column using n-propanol-water mixture (7:3 parts by volume) as the elutant. The chromatographic purity of the substance was tested with the same fluid on silica gel-G plates (Rf value of the Silybin dimer = 0.89). Detection was performed with 2,4-dinitrophenylhydrazine. The melting range of the substance amounts to 227°–235° C.

Figure 2:
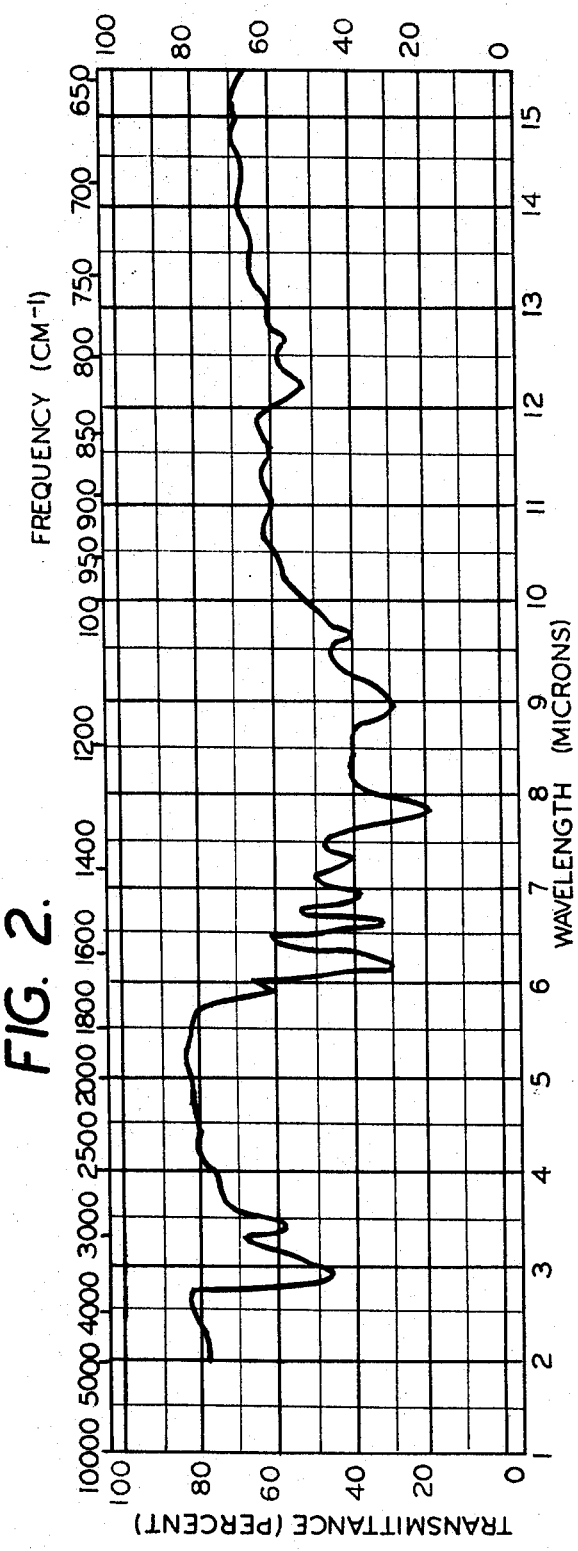

The ultraviolet and infrared spectra of this dimeric compound are represented in the drawings in which
FIG. 1 is the ultraviolet spectrum of the dimer; and
FIG. 2 is the infrared spectrum of the dimer.

EXAMPLE 2

Preparation of the Dimer of Silybin 10 g of Silybin was dissolved in 500 ml of tetrahydrofuran and 900 ml of 12N sulfuric acid was added. The reaction mixture was let stand for 14 days at room temperature and then 5 liters of water were added. The precipitated product was easily removed by filtration. It was washed acidfree with water and dried under reduced pressure at 40° C. After refinement, as described under Example 1, a molecular weight of 986 was found osmometrically in acetone.

| Testing of anti-phalloidin action on female mice | | | | | |
|---|---|---|---|---|---|
| Treatment: | | 1 × i.v. = (one dose intravenously) | | | |
| Damage: | | 3 mg/kg phalloidin I.P. 1 hour after treatment | | | |
| Substance | Dose in mg/kg I.V. | Silybin content mg/kg | n* | Mortality Rate % | Survival time /min. |
| MG (Control)** | 21.8 | — | 20 | 85 | 148.7 ± 10.7 |
| SIMG 11 Silybin MG | 140.5 | 100 Silybin | 20 | 30 | 291.0 |
| SIP MG 16 Silybin dimer MG | 22.0 | 10 Silybin dimer | 20 | 0 | — |
| SIP MG 16 Silybin dimer MG | 11.0 | 5 Silybin dimer | 20 | 10 | 310 |
| SIP MG 118 Silybin trimer MG | 31.8 | 10 Silybin trimer | 20 | 0 | — |
| SIP MG 118 Silybin trimer MG | 15.9 | 5 Silybin trimer | 20 | 5 | 226 |

*n = number of animals
**N-methylglucamine salt

EXAMPLE 3

Figure 4:
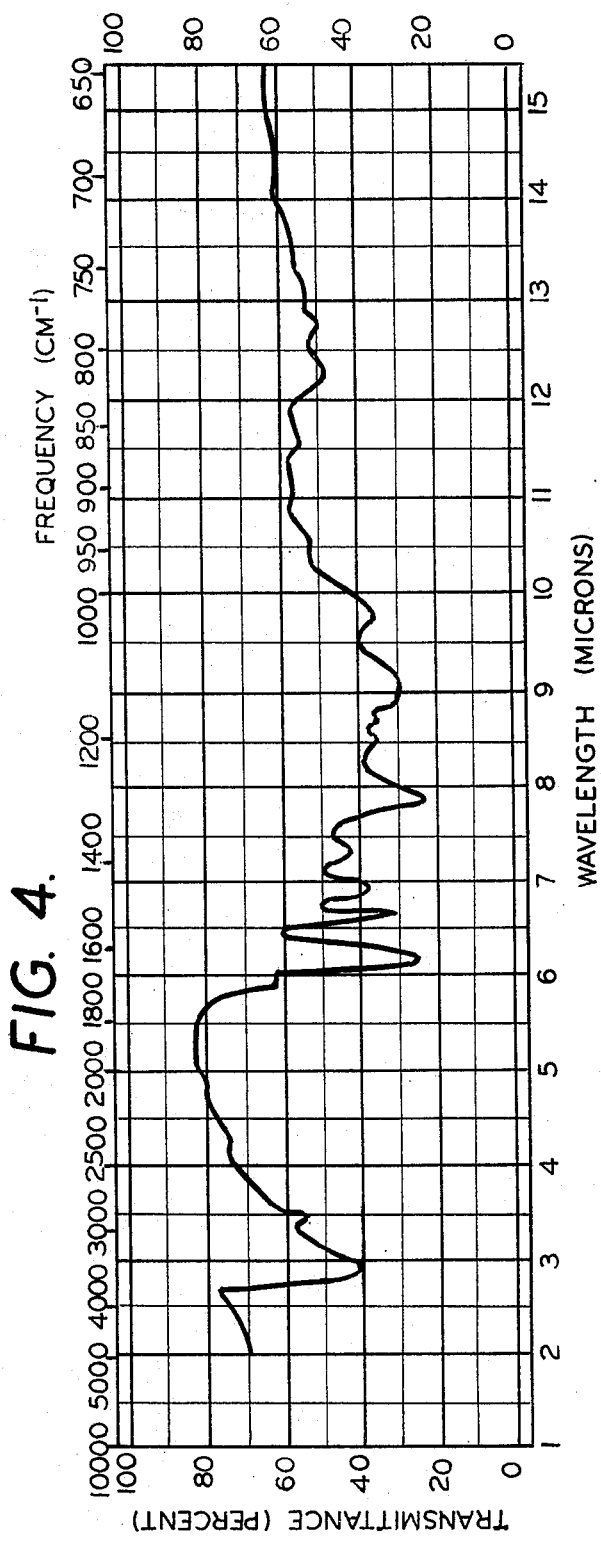
Figure 3:
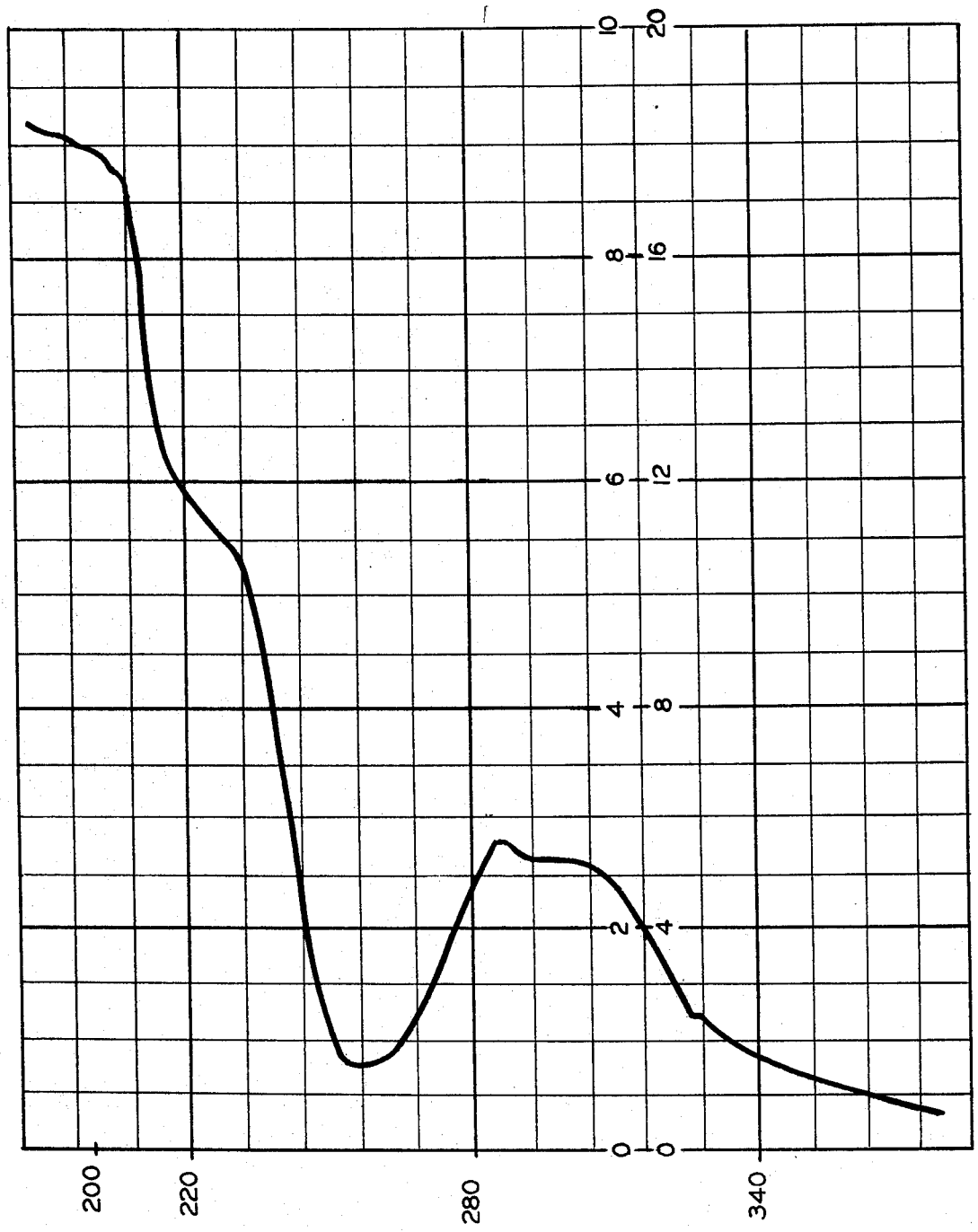

Preparation of the Trimer of Silybin 10 go of monomeric Silybin was dissolved in 500 ml of dioxane, 700 ml of 32% hydrochloric acid was added, and the mixture was let stand for 24 days at room temperature. The precipitate formed after the addition of 3 liters of water was separated by filtration, washed acid-free with water, and dried under reduced pressure at 40°–50° C. Further refinement can be performed either by reprecipitation from an acetone-water mixture or by chromatography on a silica gel-G column using a mixture of n-propanol and water of 7:3 parts by volume as the elutant. The molecular weight, as determined by osmometric measurement in acetone, amounted to 1507 (theoretically 1443.5 for Silybin trimer). Thin layer chromatography was performed in the manner described in the case of Silybin dimer in Example 1; the Rf value for the Silybin trimer was 0.82. The melting range was 247°–253° C. The ultraviolet and infrared spectra of this trimeric compound are represented in FIGS. 3 and 4.

EXAMPLE 4

Preparation of the N-Methylglucamine Salt of the Dimer of Silybin

A water-soluble N-methylglucamine salt of the dimer of silybin is obtained by the use of 6x molar amount of N-methylglucamine to 1 mole of Silybin dimer. To this end 9.63 g of Silybin dimer is dissolved with 11.7 g of N-methylglucamine in 1.5 liters of methanol, with heating. Then the solvent is completely removed by distillation under reduced pressure, and the residue is dried in the vacuum dryer at a maximum of 45° C. The product is soluble in water having a pH value of 10.0 to 11.0, but it can be dissolved in physiological saline solution only in the presence of 4% polyvinylpyrrolidone (PVP) K 15 (with respect to the saline solution). Such a physiological solution is stable for a long time at a pH value adjusted to 7.5 to 8.0, in the presence of 4% PVP.

EXAMPLE 5

Preparation of the N-Methylglucamine Salt of the Trimer of Silybin

For the preparation of a water-soluble N-methylglucamine salt, 18 moles of N-methylglucamine are required for each mole of Silybin trimer. 14.43 g of Silybin trimer is dissolved together with 35.1 g of N-methylglucamine in 1.5 liters of methanol. The rest of the procedure is the same as described with reference to the preparation of the N-methylglucamine salt of the dimer of Silybin. The product dissolves in water having a pH of 10.0 to 11.0 and is stable for a long time in physiological saline solution in the presence of 4% PVP at a pH adjusted to 7.5 to 8.0, without the occurrence of turbidity.

THERAPEUTIC PREPARATIONS

EXAMPLE A

Tablets and Dragées 10.000 kg of Silybin dimer in one case and 22,150 kg of Silybin dimer as N-methylglucamine salt in the other are mixed with the following adjuvants and granulated:
  6.0 kg of microcrystalline cellulose
  10.6 kg of Amylum tritici
  206.750 kg of lactose (or 184.500 kg in the case of the N-methylglucamine salt)
  5.0 kg PVP
To the dried granule are added the following:
  4.00 kg of microcrystalline cellulose
  3.25 kg of silicon dioxide
  5.00 kg of stearic acid.

From the mixture tablets were pressed weighing 250.0 mg each (containing 10.0 mg of Silybin dimer or 22.15 mg of Silybin dimer as the N-methylglucamine salt). These tablets can serve, if desired, as cores for the preparation of dragées. In this case they are coated with the following candy-coating suspension by the conventional method:
  Gum arabic: 5.95 kg
  Talc: 81.55 kg
  Chocolate: 2.63 kg
  Sienna: 12.50 kg
  Saccharose: 97.37 kg
The final weight of a dragée amounts to 450.0 mg.

EXAMPLE B

Tablets and Dragées 10.000 kg of Silybin dimer in one case and 22.150 kg of N-methylglucamine salt of Silybin dimer in the other are mixed with the following substances:
  70.0 kg of glucose
  25.0 kg of amylum tritici
  5.0 kg of sorbitol
  1.5 kg of polyethyleneglycol-sorbitanum oleinicum
  6.0 kg of stearic acid
  132.5 kg of lactose (120.350 kg in the case of the N-methulglucamine salt of Silybin dimer)

This mixture is compressed to form tablets each having a weight of 250 mg (containing 10.0 mg of Silybin dimer in the one case and 22.15 mg of Silybin dimer as N-methylglucamine salt in the other. The compressed tablets can serve, if desired, as cores for dragées, as cores for dragées, using 200 kg of the above-specified candy coating suspension, so that the dragées will weight approximately 450 mg each.

EXAMPLE C

Suppositories 0.04 kg of Silybin dimer in one case and 0.089 kg of the N-methylglucamine salt of Silybin dimer in the other are mixed with stirring with 1.960 kg and 1.911 kg, respectively, of melted DAB 7 hard fat, and suppositories are cast from this composition. Each 2.0 gram suppository contains 40 mg of Silybin dimer or 89 mg of Silybin dimer in the N-methylglucamine salt form, as the case may be.

EXAMPLE D

Drops

In 69.795 kg and 69.430 kg, respectively, of demineralized water, the following are successively dissolved:
  1.000 kg of polyvinylpyrrolieone (mol.wt. = 10,000)
  0.300 kg of Silybin dimer in the one case and 0.665 kg of the N-methylglucamine salt of Silybin dimer in the other case
  0.200 kg of potassium sorbate
  0.015 kg of saccharin.
Then the following are added:
  28.570 kg of "Karion F," fluid
  0.100 kg of chocolate flavoring
  0.020 kg of peppermint flavoring.
  20 drops contain 3 mg of Silybin dimer or 6.65 mg of the N-methylglucamine salt of Silybin dimer, as the case may be.

EXAMPLE E

Ampoules

For the preparation of 10,000 ampoules, 0.315 kg of N-mehtylglucamine salt of Silybin dimer is dissolved in 49.685 liters of physiological saline solution to which 4% polyvinylpyrrolidone (j.wt. 10,000) has been added. The pH value is not to fall below 7.6. The solution is sterile-filtered and poured into sterile brown 5-ml. ampoules, so that the content per ampoule will be 31.5 mg of N-methylflucamine salt.

The preceding data are also applicable to Silybin trimer and the other oligomers.

It will be appreciated that the instant specification and examples are set forth by way of illustration and not limitation, and that various modifications and changes may be made without departing from the spirit and scope of the present invention.

What is claimed is:

1. Polymeric Silybin having a degree of polymerization $n = 2$ to 8.
2. Polymeric Silybin as claimed in claim 1 in its salt form.
3. Dimeric Silybin as claimed in claim 1.
4. Trimeric Silybin as claimed in claim 1.
5. N-methylglucamine salt of dimeric Silybin as claimed in claim 3.
6. N-methylglucamine salt of trimeric Silybin as claimed in claim 4.
7. Process for preparing polymeric Silybin as claimed in claim 1 which comprises polymerizing Silybin in the presence of an aqueous mineral acid in an organic solvent system in which Silybin is sufficiently soluble, in the presence of aqueous mineral acid, that no precipitation of the monomeric starting product occurs during polymerization.
8. Process as claimed in claim 7 wherein the solvent system comprises at least one of cyclic ethers, dioxane or tetrahydrofuran.
9. Process as claimed in claim 7 wherein the mineral acid is hydrochloric acid.
10. Process as claimed in claim 7 wherein the mineral acid is sulfuric acid.
11. Process as claimed in claim 7 wherein the solvent system comprises dioxane and the aqueous mineral acid is hydrochloric acid.
12. Therapeutic composition comprising a pharmaceutically acceptable carrier and hepotophylactically effective amounts of polymeric Silybin having a degree of polymerization $n = 2$ to 8 as claimed in claim 1.
13. Therapeutic composition as claimed in claim 12 wherein said polymeric Silybin is a dimer or trimer of Silybin.
14. Therapeutic composition as claimed in claim 12 wherein said polymeric Silybin is in the form of its N-methylglucamine salt.

* * * * *